United States Patent
Ditter et al.

(10) Patent No.: US 12,342,998 B2
(45) Date of Patent: Jul. 1, 2025

(54) SENSOR ENABLED LEFT ATRIAL APPENDAGE OCCLUSION SYSTEM FOR THREE-DIMENSIONAL IMAGING AND METHOD THEREOF

(71) Applicant: Coherex Medical, Inc., Salt Lake City, UT (US)

(72) Inventors: Tom Ditter, Mission Viejo, CA (US); Kristine B. Fuimaono, Costa Mesa, CA (US)

(73) Assignee: Coherex Medical, Inc., Salt Lake City, UT (US)

( * ) Notice: Subject to any disclaimer, the term of this patent is extended or adjusted under 35 U.S.C. 154(b) by 234 days.

(21) Appl. No.: 17/733,946

(22) Filed: Apr. 29, 2022

(65) Prior Publication Data

US 2023/0346360 A1    Nov. 2, 2023

(51) Int. Cl.
*A61B 17/00*    (2006.01)
*A61B 1/00*    (2006.01)
(Continued)

(52) U.S. Cl.
CPC ...... *A61B 17/0057* (2013.01); *A61B 1/00193* (2013.01); *A61B 5/062* (2013.01);
(Continued)

(58) Field of Classification Search
CPC ............ A61B 5/062; A61B 2034/2051; A61B 5/6867; A61B 2017/00632; A61B 2017/00623; A61B 17/0057; A61B 5/6852

See application file for complete search history.

(56) References Cited

U.S. PATENT DOCUMENTS 5,391,199 A    2/1995    Ben-Haim
5,443,489 A    8/1995    Ben-Haim
(Continued)

FOREIGN PATENT DOCUMENTS

CN    204909546 U    * 12/2015
CN    209595820        11/2019
(Continued)

OTHER PUBLICATIONS

L. Weihe, "Watchman Device (Left Atrial Appendage Closure)", 2019 (Year: 2019).*
(Continued)

*Primary Examiner* — Joel Lamprecht
*Assistant Examiner* — Nyrobi Celestine
(74) *Attorney, Agent, or Firm* — David L. Stott

(57) ABSTRACT

Medical devices, systems and methods for occluding a left atrial appendage of a heart with an implantable medical device and three-dimensional imaging. In one embodiment, the imaging is facilitated with a controller coupled to one or more magnetic field generators and a display, the one or more magnetic field generators configured to generate a magnetic field within the anatomy of a patient and the display provides the imaging and display information thereon. The medical system also includes a medical device delivery system for delivering the implantable medical device. The medical device includes one or more magnetic field location sensors therewith that are operatively coupled to the controller. With this arrangement, the sensors are sized and configured to facilitate providing the three-dimensional imaging within the heart that is viewable on the display to assist a physician to safely and effectively implant the medical device.

15 Claims, 8 Drawing Sheets

(51) Int. Cl.
*A61B 5/06* (2006.01)
*A61B 34/20* (2016.01)

(52) U.S. Cl.
CPC .... *A61B 34/20* (2016.02); *A61B 2017/00623* (2013.01); *A61B 2017/00632* (2013.01); *A61B 2034/2051* (2016.02)

(56) References Cited

U.S. PATENT DOCUMENTS

| | | | |
|---|---|---|---|
| 5,558,091 | A | 9/1996 | Acker et al. |
| 5,944,022 | A | 8/1999 | Nardella et al. |
| 5,983,126 | A | 11/1999 | Wittkampf |
| 6,172,499 | B1 | 1/2001 | Ashe |
| 6,177,792 | B1 | 1/2001 | Govari et al. |
| 6,266,551 | B1 | 7/2001 | Osadchy et al. |
| 6,456,828 | B1 | 9/2002 | Ozluturk |
| 6,690,963 | B2 | 2/2004 | Ben-Haim et al. |
| 6,788,967 | B2 | 9/2004 | Ben-Haim et al. |
| 8,498,691 | B2 | 7/2013 | Moll et al. |
| 9,649,115 | B2 | 5/2017 | Edmiston et al. |
| 10,136,828 | B2 | 11/2018 | Houben et al. |
| 10,631,969 | B2 | 4/2020 | Edmiston et al. |
| 11,173,287 | B2 | 11/2021 | Eliyahu et al. |
| 2007/0123934 | A1* | 5/2007 | Whisenant ......... A61B 17/0057 606/213 |
| 2008/0221566 | A1* | 9/2008 | Krishnan ............ A61B 34/20 606/41 |
| 2015/0335383 | A9* | 11/2015 | Cohen ................ A61B 34/73 606/41 |
| 2017/0340334 | A1* | 11/2017 | Miles .............. A61B 17/12172 |
| 2018/0078172 | A1* | 3/2018 | Kusumoto ............ A61B 5/062 |
| 2020/0155164 | A1* | 5/2020 | Edmiston ......... A61B 17/12177 |
| 2020/0205738 | A1* | 7/2020 | Adawi .................. A61B 5/028 |
| 2021/0106809 | A1* | 4/2021 | Solem .................. A61F 2/2409 |
| 2021/0196394 | A1* | 7/2021 | Govari ............. A61M 25/0662 |
| 2021/0401418 | A1* | 12/2021 | Dang ................. A61B 5/0215 |
| 2022/0000445 | A1* | 1/2022 | Datta ................... A61B 8/5261 |
| 2022/0054803 | A1* | 2/2022 | Eliyahu .......... A61M 25/0662 |
| 2022/0192753 | A1* | 6/2022 | Rosenberg ............ A61B 90/37 |
| 2023/0044012 | A1* | 2/2023 | Ben-Haim ............ A61B 5/065 |

FOREIGN PATENT DOCUMENTS

| | | |
|---|---|---|
| DE | 102009007214 | 9/2010 |
| DE | 102009016481 | 10/2010 |

OTHER PUBLICATIONS

R. Sommer et al, "Conformal Left Atrial Appendage Seal Device for Left Atrial Appendage Closure: First Clinical Use", JACC: Cardiovascular Interventions, vol. 14, No. 21, pp. 2368-2374, Aug. 2021 (Year: 2021).*

* cited by examiner

SENSOR ENABLED LEFT ATRIAL APPENDAGE OCCLUSION SYSTEM FOR THREE-DIMENSIONAL IMAGING AND METHOD THEREOF

TECHNICAL FIELD

The present invention relates generally to the occlusion of tissue openings or appendages and, more specifically, to devices, systems and methods for implanting medical devices with three-dimensional imaging.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages do not appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, it can be difficult to ensure the medical device is appropriately sized, oriented and positioned relative to the ostium of the left atrial appendage. As such, it would be advantageous to provide a percutaneous system, method and/or device that addresses, for example, the issues relating to the size of the medical device as well as its position and orientation within the ostium of the left atrial appendage.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods for delivering a medical device with an imaging system. In one embodiment, a medical system for generating three-dimensional imaging within a heart of a patient is provided. The medical system includes a controller, a sheath, a pusher catheter, and one or more magnetic field location sensors. The controller is coupled to one or more magnetic field generators and a display, the one or more magnetic field generators configured to generate a magnetic field within the anatomy of the patient and the display for providing display information thereon. The sheath extends with a longitudinal length and a lumen defined along the longitudinal length of the sheath. The pusher catheter includes a handle and an implantable medical device, the implantable medical device removably coupled adjacent a distal end of the pusher catheter. The pusher catheter and the implantable medical device are moveable through the lumen of the sheath such that the implantable medical device is moveable between a constricted position and an expanded position. The one or more magnetic field location sensors are associated with the implantable medical device and operatively coupled to the controller. With this arrangement, the one or more magnetic field location sensors are sized and configured to facilitate providing the three-dimensional imaging within the heart so as to be viewable on the display.

In another embodiment, the one or more magnetic field location sensors are positioned along a tissue growth member of the implantable medical device, the tissue growth member extending with an external surface and an inner portion, the external surface of the tissue growth member configured to directly contact tissue within the left atrial appendage, the one or more magnetic field location sensors positioned along the inner portion of the tissue growth member. In another embodiment, the one or more magnetic field location sensors are directly positioned on at least one of the implantable medical device, the pusher catheter, and the sheath.

In another embodiment, the one or more magnetic field location sensors are operatively coupled to the controller with at least one of a wire connection and a wireless connection. In still another embodiment, the handle of the pusher catheter includes a release mechanism to facilitate releasing the implantable medical device from the distal end of the pusher catheter to permanently implant the implantable medical device within the heart. In another embodiment, upon the implantable medical device being removed from the pusher catheter such that the implantable medical device is implanted in the heart, the one or more magnetic field location sensors associated with the implantable medical device is activatable wirelessly.

In accordance with another embodiment of the present invention, a medical system for generating three-dimensional imaging within a heart of a patient is provided. The medical system includes a controller and a medical device delivery system. The controller is coupled to one or more magnetic field generators and a display, the one or more magnetic field generators are configured to generate a magnetic field within the anatomy of the patient and the display for providing display information thereon. The medical device delivery system includes a sheath, a pusher catheter and an implantable medical device, the sheath extending with a central lumen sized and configured to advance the pusher catheter and the implantable medical device therethrough. The pusher catheter includes a handle coupled to a proximal end of the pusher catheter. The implantable medical device is removably coupled adjacent a distal end of the pusher catheter, the implantable medical device including one or more magnetic field location sensors positioned therewith and operatively coupled to the controller. With this arrangement, the one or more magnetic field location sensors are sized and configured to facilitate providing the three-dimensional imaging within the heart viewable on the display.

In another embodiment, the pusher catheter includes one or more second magnetic field location sensors associated therewith, the one or more second magnetic field location sensors are coupled to the controller and are positioned adjacent a distal end portion of the pusher catheter. In still another embodiment, the sheath includes one or more third magnetic field location sensors associated therewith, the one or more third magnetic field location sensors are coupled to the controller and are positioned adjacent a distal end portion of the sheath. In still another embodiment, the one or more magnetic field location sensors are positioned along a tissue growth member of the implantable medical device, the tissue growth member extending with an external surface and an inner portion, the external surface of the tissue growth member configured to directly contact tissue within the left atrial appendage, the one or more magnetic field location sensors positioned along the inner portion of the tissue growth member.

In another embodiment, the one or more magnetic field location sensors are operatively coupled to the controller with at least one of a wire connection and a wireless connection. In yet another embodiment, the handle of the pusher catheter includes a release mechanism to facilitate releasing the implantable medical device from the distal end of the pusher catheter to permanently implant the implantable medical device within the heart. In another embodiment, upon the implantable medical device being removed from the pusher catheter such that the implantable medical device is implanted in the heart, the one or more magnetic field location sensors associated with the implantable medical device is activatable wirelessly.

In accordance with another embodiment of the present invention, a method for obtaining three-dimensional imaging within a left atrium and left atrial appendage of a heart is provided. The method includes the steps of: generating a magnetic field within the anatomy of a patient with one or more magnetic field generators positioned adjacent the patient; advancing a medical device delivery system through a vasculature of the patient and toward the heart of the patient, the medical device delivery system sized and configured to deliver an implantable medical device in the left atrial appendage of the heart with a pusher catheter; activating one or more magnetic field location sensors associated with the medical device delivery system for obtaining the three-dimensional imaging within the left atrium; deploying the implantable medical device adjacent the left atrial appendage; viewing the three-dimensional imaging of the left atrium on a display of a control console operatively coupled to the magnetic field generators and the medical device delivery system; securing the implantable medical device to tissue with anchoring tines adjacent to or within the left atrial appendage of the heart; and releasing the pusher catheter of the delivery system from the implantable medical device to permanently leave the medical device adjacent to or within the left atrial appendage of the heart.

In one embodiment, the step of activating includes wirelessly activating the one or more magnetic field location sensors. In another embodiment, the step of activating includes activating one or more magnetic field location sensors directly positioned on at least one of the implantable medical device, the pusher catheter, and a sheath of the medical device delivery system. In another embodiment, subsequent to the releasing step includes the step of activating the one or more magnetic field location sensors associated with the implantable medical device wirelessly. In still another embodiment, the step of deploying includes deploying the implantable medical device with a tissue growth member therewith, the one or more magnetic field location sensors positioned along an inner portion of the tissue growth member.

In accordance with another embodiment of the present invention, a method of obtaining three-dimensional imaging of structure within a left atrium and left atrial appendage of a heart is provided. The method includes the steps of: positioning a sheath distal end of a sheath within the left atrium of the heart so that the sheath extends along the vasculature extending to the heart, the sheath extending with a longitudinal length and defining a lumen along the longitudinal length of the sheath; advancing a medical device with a catheter of a delivery system through the lumen of the sheath so that the medical device is in a constricted position adjacent the sheath distal end, the medical device coupled adjacent to a distal end of the catheter and the medical device associated with one or more magnetic field location sensors integrated therewith; deploying the medical device from the sheath distal end so that the medical device and the one or more magnetic field location sensors are positioned adjacent the left atrial appendage; activating the one or more magnetic field location sensors to obtain imaging of the structure within the left atrium of the heart; securing the medical device to tissue adjacent to or within the left atrial appendage of the heart; and releasing the catheter of the delivery system from the medical device to permanently leave the medical device and the one or more magnetic field location sensors adjacent to or within the left atrial appendage.

In another embodiment, the activating includes wirelessly activating the one or more magnetic field location sensors. In still another embodiment, the activating includes activating one or more magnetic field location sensors directly positioned on at least one of the implantable medical device, the catheter, and the sheath of the medical device delivery system. In another embodiment, subsequent to the releasing includes activating the one or more magnetic field location sensors associated with the implantable medical device wirelessly. In yet another embodiment, the deploying includes deploying the implantable medical device with a tissue growth member therewith, the one or more magnetic field location sensors positioned along an inner portion of the tissue growth member.

In a further embodiment, the method includes deactivating the one or more magnetic field location sensors subsequent to the releasing step and withdrawing the catheter and delivery system from the vasculature. In another embodiment, subsequent to the withdrawing the catheter and the delivery system from the vasculature, the method further includes wirelessly re-activating the one or more magnetic field location sensors to obtain imaging of some of the structure within the heart. In another embodiment, the deploying includes deploying an occluder portion of the medical device and separately deploying an anchor portion of the medical device.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
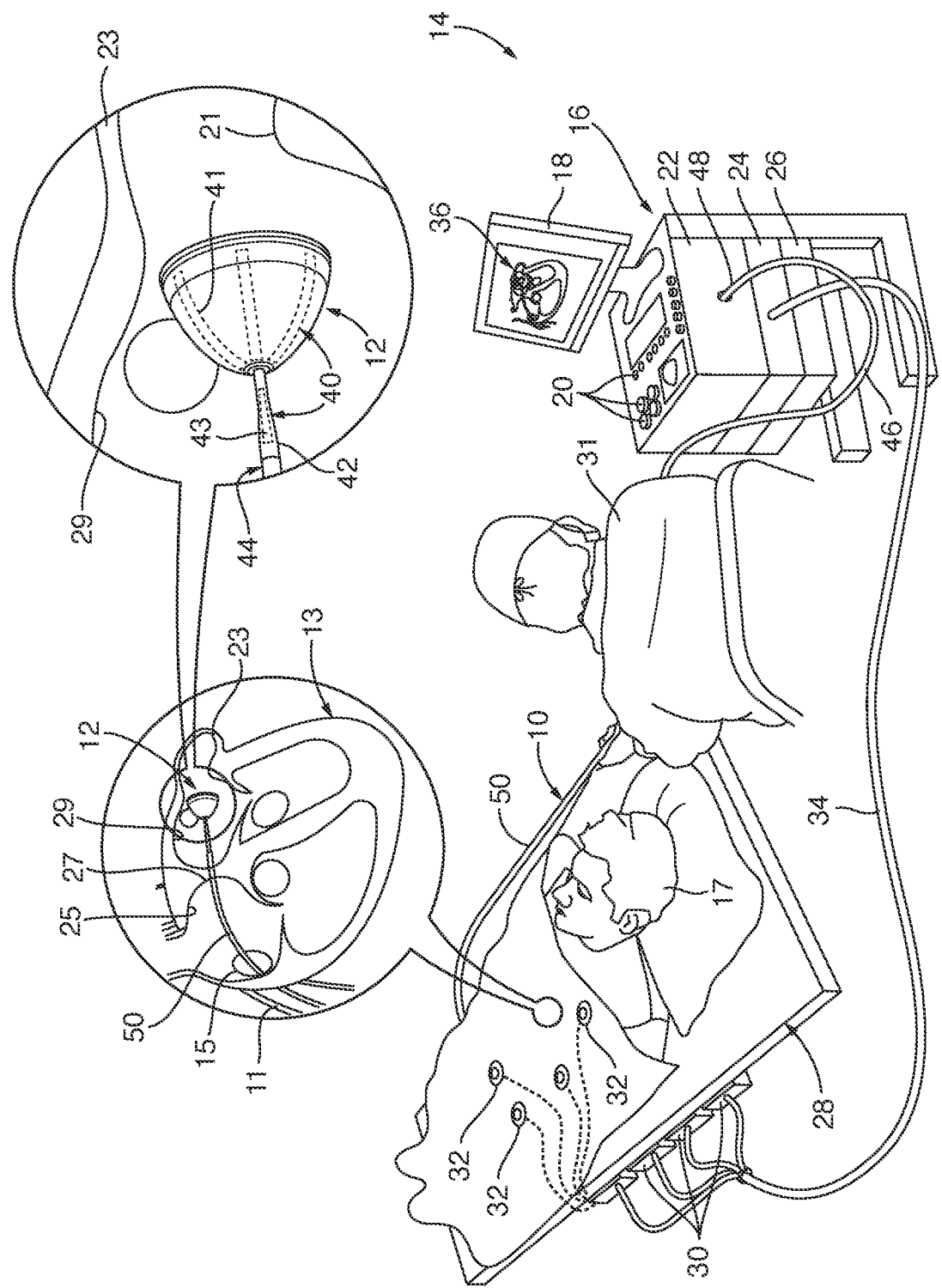
FIG. 1 is a perspective view that illustrates a medical system for navigating a medical device delivery system with 3-D imaging associated with the medical system, depicting an implantable medical device of the delivery system within the left atrium, according to an embodiment of the present invention.
Figure 5:
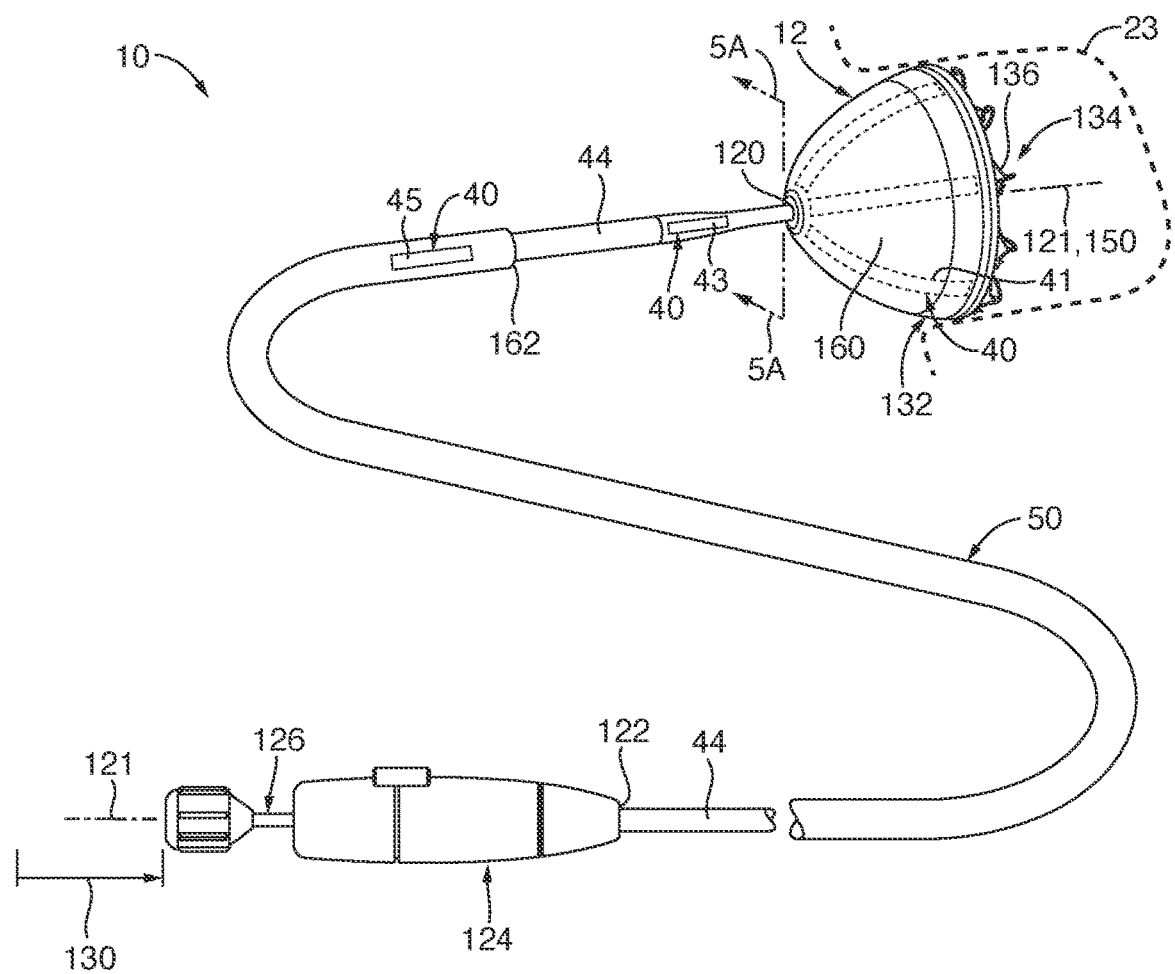
FIG. 5 is a perspective view of the medical device delivery system, depicting the medical device in a deployed position with anchors in an engageable position, according to another embodiment of the present invention.

Referring to FIGS. 1 and 5, a medical device delivery system 10 sized and configured to deliver a medical device 12 through the vasculature 11 and into the heart 13 via, for example, the inferior vena cava 15, for implanting the medical device in the heart 13 of a patient 17. In one embodiment, the medical device delivery system 10 may be employed with a medical system 14 and one or more sensors associated therewith that may facilitate three-dimensional ("3-D") imaging of the anatomy adjacent to and surrounding the medical device 12. Such 3-D imaging of the anatomy adjacent to the medical device 12 may assist the physician to optimize the position and orientation of the medical device 12 relative to a landing zone in the anatomy, such as the ostium 21 at the entrance of the left atrial appendage 23 of the heart 13, to assist in optimally anchoring and implanting the medical device 12 within the anatomy. Further, in another embodiment, subsequent to implanting the medical device 12 in the patient's anatomy, the physician may activate the one or more sensors associated with the medical device 12 wirelessly to view the progress of the implanted medical device 12 within the anatomy and how the implant may be integrating with the tissue. In this manner, a physician may employ 3-D imaging to implant the medical device 12 as well as monitor the status of the medical device 12 in subsequent follow-up visits with the patient 17, and obtain helpful information and data of the implanted medical device 12 and how it's integrating with the tissue in, for example, the heart 13.

With reference to FIG. 1, embodiments disclosed herein provide the medical device delivery system 10, which may be a tool or part of a tool, of the medical system 14 used to generate and display information (e.g., a chart, anatomical models of a portion of a patient and signal information). In some embodiments, the medical system 14 may be an electromagnetic navigation system used to determine the location of the medical device delivery system 10 and/or the medical device 12 in 3-D space during a medical procedure. During these medical procedures, various components of the medical device delivery system 10 and the medical system 14 may generate and transmit signals (e.g., electrical signals based on the amplitude and phase of magnetic fields) to facilitate the determination of the locations of anatomy and portions of the medical device delivery system 10 relative to the anatomy.

In one embodiment, the medical system 14 may include controller or a control console 16 with a display 18, an input device 20, a driver circuit 22, a signal processor 24, and memory 26. Further, the medical system 14 may include a patient platform 28, field generators 30, and body surface electrodes 32 each coupled to the control console 16 with connector wire 34. FIG. 1 provides an illustration of an example medical system 14 which may be used to generate and display information 36 (e.g., a chart, anatomical models of a portion of a patient and signal information). The medical system 14 and the medical device delivery system 10 shown in FIG. 1 are merely by way of example. For example, the implantable medical device 12 can be any type of implantable medical device, such as implantable medical devices for closing septal deflects or other defect in the heart. Further, other types of implantable medical devices delivered via a sheath and/or catheter for delivering and implanting devices to other body organs or within the vasculature may also be employed with the medical system 14 and an implant delivery system as set forth herein.

In one embodiment, a physician may insert the medical device delivery system into a portion of a patient anatomy, such as the vascular system of the patient 17, so that the medical device 12 of the medical device delivery system 10 enters a right atrium 25, crosses the septum 27 to enter the left atrium 29 of the heart 13. The control console 16 may use magnetic position sensing to determine 3-D position coordinates of the medical device delivery system 10 (e.g., coordinates of the medical device 12) inside the heart 13. To determine the position coordinates, a driver circuit 22 in the control console 16 may drive, via connector 34, field generators 30 to generate magnetic fields within the anatomy of the patient 17.

The field generators 30 include one or more emitter coils (not shown in FIG. 1), placed at known positions external to the patient 17, which are configured to generate magnetic fields in a predefined working volume that contains a portion of the pre-defined interest of the patient anatomy, such as the left atrium 29 of the heart 13. Each of the emitting coils may be driven by a different frequency to emit a constant magnetic field. For example, in the example medical system 14 shown in FIG. 1, one or more emitter coils can be placed below the torso of the patient 17 and each configured to generate magnetic fields in a predefined working volume that contains the heart 13 of the patient 17.

Further, as shown in FIG. 1, one or more magnetic field location sensors 40 may be associated with the medical device delivery system 10. The medical device delivery system 10 may include one or more first magnetic field location sensors 41, one or more second magnetic field location sensors 43, and/or one or more third magnetic field location sensors 45 (see FIGS. 3, 4 and 5). The first magnetic field location sensors 41 may be disposed on the implantable medical device 12. The second magnetic field location sensors may be integrated with a distal end portion 42 of a pusher catheter 44 of the medical device delivery system 10 (see also, FIGS. 4 and 5). The third magnetic field location sensors 45 may be integrated with an end portion 180 of a sheath 50 (see FIGS. 3-5). As such, any one of the first, second and third magnetic field location sensors 41, 43, 45 of the one or more magnetic field location sensors 40 may be associated with various portions of the medical device delivery system 10. The one or more magnetic field location sensors 40 may be sized and configured to generate electrical signals, based on the amplitude and phase of the magnetic fields, indicating the 3-D position coordinates of the medical device 12 and/or the distal end portion 42 of the pusher catheter 44, or other portions of the medical device delivery system 10, such as the sheath 50 of the delivery system 10. The electrical signals may be communicated to the control console 16 to determine the position coordinates of the tool. The electrical signals may be communicated to the control console 16 via a wire 46.

Alternatively, or in addition to wired communication, the electrical signals may be wirelessly communicated to the control console 16, for example, via a wireless communication interface (not shown) at the medical device 12 that may communicate with input/output (I/O) interface 48 in the control console 16. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 48 may operate in accordance with any suitable wireless communication standard that is known in the art, such as for example, IR, RF, Bluetooth, one of the IEEE 802.11 family of standards (e.g., Wi-Fi), or the HiperLAN standard.

Figure 5A:
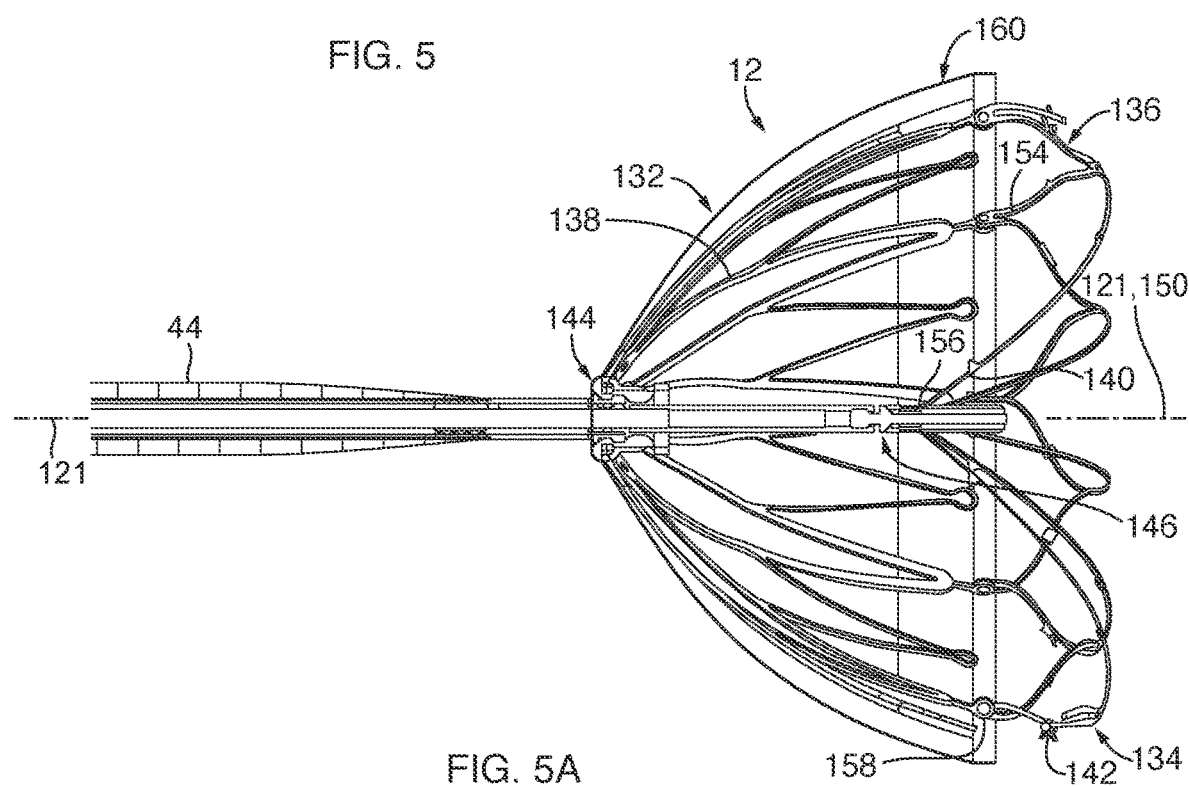
FIG. 5A is a cross-sectional view of the medical device coupled to the delivery system taken along section line 5A-5A in FIG. 5, according to another embodiment of the present invention.

Although FIG. 1 shows a single or minimal number of magnetic field location sensors 40 disposed at the medical device 12, the medical device delivery system 10 may include one or more magnetic field location sensors 40 each disposed at any portion of the medical device delivery system, as previously set forth, such as the distal end portion 42 of the pusher catheter 44 and/or a sheath 50 and/or along a framework 136, primary hub 144, and/or secondary hub 146 of the medical device 12 (see FIG. 5A). The one or more magnetic field location sensors 40 may include one or more miniature coils (not shown). For example, the one or more magnetic field location sensors 40 may include multiple miniature coils oriented along different axes. Alternatively, the magnetic field location sensors 40 may comprise either another type of magnetic sensor or position transducers of other types, such as impedance-based or ultrasonic location sensors.

The medical system 14 may include one or more signal processors 24 configured to process the signals to determine the position coordinates of portions of the medical device delivery system 10, such as the medical device 12, including both location and orientation coordinates. The method of position sensing described hereinabove is implemented in the CARTO mapping system produced by Biosense Webster Inc., of Diamond Bar, Calif., and is described in detail in the patents and the patent applications cited herein. Further, a similar medical system configured to map anatomy and positionally locate medical devices relative to the mapped anatomy is disclosed in U.S. Pat. Nos. 11,173,287 and 10,136,828, the disclosures of which are incorporated herein by reference in their entirety.

Further, although the example medical system 14 may be configured to measure the position of the medical device 12 and/or other portions of the medical device delivery system 10 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 48 may enable the control console 16 to interact with the medical device delivery system 10, the body surface electrodes 32 and any other sensors (not shown). Based on the electrical impulses received from the body surface electrodes 32 and the electrical signals received from the one or more magnetic field location sensors 40 of the medical device delivery system 10 via the I/O interface 48 and other components of the medical system 14, the signal processor 24 may determine the location of, for example, the medical device 12 in a 3-D space and generate the display information 36, which may be shown on the display 18.

The signal processor 24 may be included in a general-purpose computer, with a suitable front end and interface circuits for receiving signals from the medical device delivery system 10 and controlling the other components of the control console 16. The signal processor 24 may be programmed, using software, to perform the functions that are described herein. The software may be downloaded to the control console 16 in electronic form, over a network, for example, or it may be provided on non-transitory tangible media, such as optical, magnetic or electronic memory media. Alternatively, some or all of the functions of the signal processor 24 may be performed by dedicated or programmable digital hardware components.

In the example shown at FIG. 1, the control console 16 may be connected, via connector wire 34, to body surface electrodes 32, each of which are attached to a patient 17 using patches (e.g., indicated in FIG. 1 as circles around the electrodes 32) that adhere to the skin of the patient. The body surface electrodes 32 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery. In addition, or alternative to the patches, body surface electrodes 32 may also be positioned on the patient 17 using articles worn by patient 17 which include the body surface electrodes 32 and may also include one or more position sensors (not shown) indicating the location of the worn article. For example, body surface electrodes 32 can be embedded in an article (e.g., a vest) disposed on the patient 17. During operation, the body surface electrodes 32 assist in providing a location of the medical device 12 in 3-D space by detecting electrical impulses generated by the polarization and depolarization of cardiac tissue and transmitting information to the control console 16, via the connector wire 34. The body surface electrodes 32 can be equipped with magnetic location tracking and can help identify and track the respiration cycle of the patient 17. In addition to or alternative to wired communication, the body surface electrodes 32 may communicate with the control console 16 and one another via a wireless interface (not shown).

During delivery of the medical device 12, the signal processor 24 may present the display information 36 and may store data representing the information 36 in the memory 26. The memory 26 may include any suitable volatile and/or non-volatile memory, such as random access memory or a hard disk drive. The physician 31 may be able to manipulate the display information 36 using one or more input devices 20. Alternatively, the medical system 14 may include a second physician that manipulates the control console 16 while the physician 31 manipulates the medical device delivery system 10. It should be noted that the configuration shown in FIG. 1 is exemplary. Any suitable configuration of the medical system 14 may be used and implemented.

Figure 2:
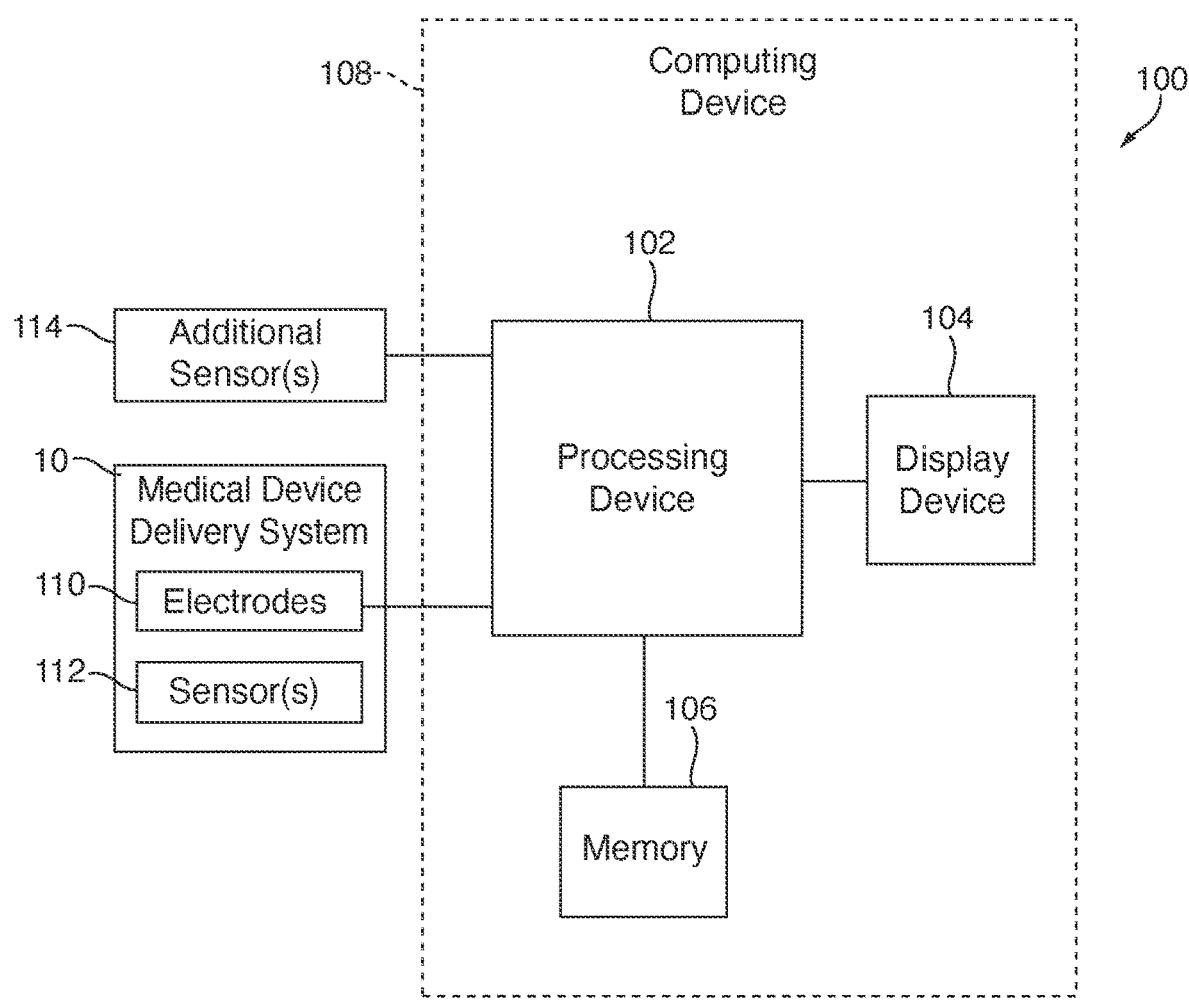
FIG. 2 is a block diagram of the medical system associated with the medical device delivery system, according to another embodiment of the present invention.

FIG. 2, in another embodiment, is a block diagram illustrating example components of a medical system 100, similar to medical system 14 of FIG. 1, for use with embodiments described herein. As shown in FIG. 2, the system 100 may be employed with the medical device delivery system 10, processing device 102, display device 104 and memory 106. The processing device 102, display device 104 and memory 106 are a part of a computing device 108. In some embodiments, the display device 104 may be separate from the computing device 108. Computing device 108 may also include an I/O interface, such as I/O interface 48 shown in FIG. 1.

The medical device delivery system 10 may include an array of electrodes 110 each configured to detect electrical activity (electrical signals) of an area of an organ (e.g., a heart) over time. When an ECG is performed, each electrode may detect the electrical activity of an area of the organ in contact with the electrode. The medical device delivery system 10 may also include a plurality of sensors 112. The sensors 112 include, for example, one or more magnetic field location sensors (e.g., sensor 40 in FIG. 1) for providing location signals to indicate the 3-D position coordinates of the medical device delivery system 10. In some embodiments, one or more additional sensors 114 that are separate from the medical device delivery system 10, as shown in example system 100, may also used to provide location signals. The additional sensors 114 may also include sensors (e.g., body surface electrodes 32 on the skin of a patient as depicted in FIG. 1) used to assist with detection of electrical activity of an organ via detection of electrical changes on the skin due to the electro-physiologic pattern of the organ, such as the heart.

The processing device 102 may include one or more processors each configured to process the ECG signals, record ECG signals over time, filter ECG signals, fractionate ECG signals into signal components (e.g., slopes, waves, complexes) and generate and combine ECG signal information for displaying the plurality of electrical signals on display device 104. The processing device 102 may also generate and interpolate mapping information for displaying 3-D maps of the heart on display device 104. The processing device 102 may include one or more processors (e.g., signal processor 24 of FIG. 1) configured to process the location information acquired from sensors (e.g., sensors 112 and additional sensors 114) to determine the position coordinates of relevant portions of the medical device delivery device 10, including both location and orientation coordinates.

In addition, processing device 102 determines locations of anatomical regions of an organ (e.g., the heart) on the map, determines which electrical signals correspond to areas of the organ that are located within the anatomical regions of the organ and generate signal information (e.g., correlated ECG information) for displaying electrical signals determined to correspond to the areas of the organ that are located within the anatomical regions of the organ (i.e., determined to be the electrical signals acquired by electrodes (i.e., poles) disposed at the corresponding areas of the organ). The processing device 102 may drive display device 104 to display dynamic maps (i.e., spatio-temporal maps) of the organ and the electrical activity of the organ using the mapping information and the signal information. The processing device 102 may also drive display device 104 to display the signals determined to be located within the anatomical region of the organ using the correlated signal information.

The display device 104 may include one or more displays each configured to display 3-D maps of the organ representing spatio-temporal manifestations of the electrical activity of the organ over time and display the electrical signals acquired from the organ over time. For example, a 3-D map of the organ representing the electrical activity of the organ for a specific time interval and the electrical signals acquired from the organ during the time interval may be displayed concurrently on the same display device 104. Alternatively, the 3-D map of the organ and the electrical signals acquired during the same time interval may be displayed on separate display devices. Furthermore, the electrodes 110, sensor(s) 112 and additional sensor(s) 114 may be in wired or wireless communication with processing device 102. As such, the display device 104 may also be in wired or wireless communication with the processing device 102.

Now with reference to FIGS. 3-5, the medical device delivery system 10 will now be described. The medical device delivery system 10 may extend longitudinally to define a central axis 121 and may be sized and configured to percutaneously move through the vasculature to deliver the implantable medical device 12 within or adjacent to, for example, the left atrial appendage 23 in the heart 13 (FIG. 1). The medical device delivery system 10 may include the implantable medical device 12, the pusher catheter 44, and the sheath 50. The pusher catheter 44 may extend between a distal end 120 and a proximal end 122, the medical device 12 being removably coupled adjacent the distal end 120 of the pusher catheter 44. The proximal end 122 of the pusher catheter 44 may be coupled to a pusher catheter handle 124. Such pusher catheter handle 124 may be sized and configured to deploy the medical device 12 from a constricted position (FIG. 3) to a deployed position (FIG. 5) such that the medical device 12 may at least partially self-expand upon being released from the sheath 50 (see FIG. 4). Such movement of the medical device 12 between the constricted and deployed positions may partially be employed with an anchor actuator 126 of the pusher catheter handle 124 such that the anchor actuator 126 may be moved between a proximal position (FIG. 4) and a distal position (FIG. 5), as shown with arrows 128 and 130, respectively. Additional disclosure of a similar medical device delivery system is disclosed in commonly assigned U.S. patent application Ser. No. 15/438,650, filed on Feb. 21, 2017, now issued as U.S. Pat. No. 10,631,969, entitled MEDICAL DEVICE FOR MODIFICATION OF LEFT ATRIAL APPENDAGE AND RELATED SYSTEMS AND METHODS, the disclosure of which is incorporated by reference herein in its entirety.

With respect to FIGS. 4, 4A, 5, and 5A, in some embodiments, the medical device 12 employed with the sheath 50 and pusher catheter 44 may include an occluder portion 132 and an anchor portion 134. Such occluder portion 132 and anchor portion 134 may be associated with a framework 136. The framework 136 may extend to define occluder frame segments 138 and anchor frame segments 140, the occluder frame segments 138 configured to support the occluder portion 132 and the anchor frame segments 140 including multiple tines 142 extending therefrom. Such tines 142 of the medical device 12 may be sized and configured to engage tissue so that the medical device 12 may be permanently implanted within the anatomy, such as the left atrial appendage 23 (depicted with dashed lines). The occluder portion 132 and the anchor portion 134 may be separately and independently deployed from the sheath 50 and the pusher catheter 44, respectively. Further, the framework 136 may extend between a primary hub 144 and a secondary hub 146 (or anchor actuating hub) such that the primary hub 144 and the secondary hub 146 may be aligned relative to each other along an axis 150, which also may be co-axial with the central axis 121 of the delivery system 10. The axis 150 defined in the medical device 12 may be defined to extend centrally and axially through the medical device 12. The secondary hub 146 may be moveable relative to the primary hub 144 so as to be moved proximally and distally along the axis 150. Such movement of the secondary hub 146 along the axis 150 may actuate the anchor portion 134 between constricted and deployed positions. The occluder frame segments 138 may extend radially and distally from the primary hub 144 such that at least some of the occluder frame segments 138 may include occluder eyelets adjacent to distal ends of the occluder frame segments 138. The anchor frame segments 140 may extend between a first end 154 and a second end 156, the first end 154 defining anchor eyelets adjacent thereto and the second end 156 being coupled to the secondary hub 146. The first end 154 of the anchor frame segments 140 may be pivotably coupled adjacent to the distal end of the occluder frame segments 138 via a pivotable interconnection 158 between the occluder eyelets and anchor eyelets of the occluder frame segments 138 and the anchor frame segments 140, respectively.

Further, the occluder frame segments 138 of the occluder portion 132 may support a tissue growth member 160. Such tissue growth member 160 may extend over and along sides of the primary hub 144 and the occluder frame segments 138. The tissue growth member 160 may be in the form of an occlusive member, but may also be in the form of a filter member, a mesh member, a membrane or any other structure, or combinations thereof, sized and configured to promote tissue in-growth therein. Further, the tissue growth member 160 may extend with multiple layers and may be formed from one or more polymeric materials, such as ePTFE ("expanded polytetrafluoroethylene") and/or a polyurethane foam, or any other suitable tissue in-growth material.

The anchor portion 134 of the medical device 12 may be actuated between a constricted position (FIG. 4A) and a deployed position (FIG. 5A) via the anchor actuator 126 associated with the pusher catheter handle 44 and via the pivotable interconnection 158 between the occluder frame segments 138 and the anchor frame segments 140. As depicted in FIGS. 4 and 4A, upon the anchor portion 134 being moved to the constricted position, the secondary hub 146 may be pulled and positioned proximally via the anchor actuator 126 being moved to the proximal position 128. Further, upon the anchor portion 134 being in the constricted position, the anchor frame segments 140 may be in a pivoted position with a portion of such anchor frame segments 140 moved within a distal end portion 42 of the pusher catheter 44 and with a portion of anchor frame segments 140 extending outside the pusher catheter 44. Upon the anchor portion 134 being moved from the constricted position (or pivoted position) to the deployed position, the anchor actuator 126 may be moved distally to the distal position 130 by manually moving the anchor actuator 126 from the proximal position 128 (FIG. 4) to the distal position 130 (FIG. 5). As depicted in FIGS. 4A and 5A, such distal movement of the anchor actuator 126 moves the secondary hub 146 distally along the axis 150 and pivotably moves the anchor portion 134 to the deployed position. In this manner, the anchor actuator 126 may be moved both proximally and distally to move the anchor portion 134 between constricted and deployed positions, respectively, or to move the anchor portion 134 between non-engaged and engaged positions (engaged positions being tines 142 engaged to tissue for anchoring the medical device 12).

Further, as previously set forth, the medical device 12 may include the one or more magnetic field location sensors 40. In one embodiment, the one or more magnetic field location sensors 40 may be associated with the tissue growth member 160 so as to define one or more first magnetic field location sensors therewith 41. In one embodiment, such one or more first magnetic field location sensors 41 may extend within the tissue growth member 160 so as to longitudinally and radially extend generally from the primary hub 144 toward a distal end of the tissue growth member 160, as generally shown with dashed lines along the tissue growth member 160 in FIGS. 1, 4 and 5. As such, the one or more first magnetic field location sensors 41 may extend in a manner to facilitate the ability to be constricted with the tissue growth member 160 within the sheath 50 as well as being deployed from the sheath as the tissue growth member 160 or occluder portion 132 self-expands and is deployed from the sheath 50, as set forth herein. In another embodiment, the one or more magnetic field location sensors may be positioned on or associated with the primary hub 144 or the secondary hub 146 of the medical device 12 or the framework 136, for example.

Furthermore, in addition to (or instead of) the first magnetic field location sensors 41, the pusher catheter 44 may include the one or more magnetic field location sensors 40 therein so as to define the before-described one or more second magnetic field location sensors 43. In one embodiment, the one or more second magnetic field location sensors 43 may be positioned adjacent the medical device 12 along the distal end portion 42 of the pusher catheter 44. In this embodiment, the one or more second magnetic field location sensors 43 may be embedded in a wall of the pusher catheter 44 so as to be exposed along an external surface of the pusher catheter 44.

Figure 3:
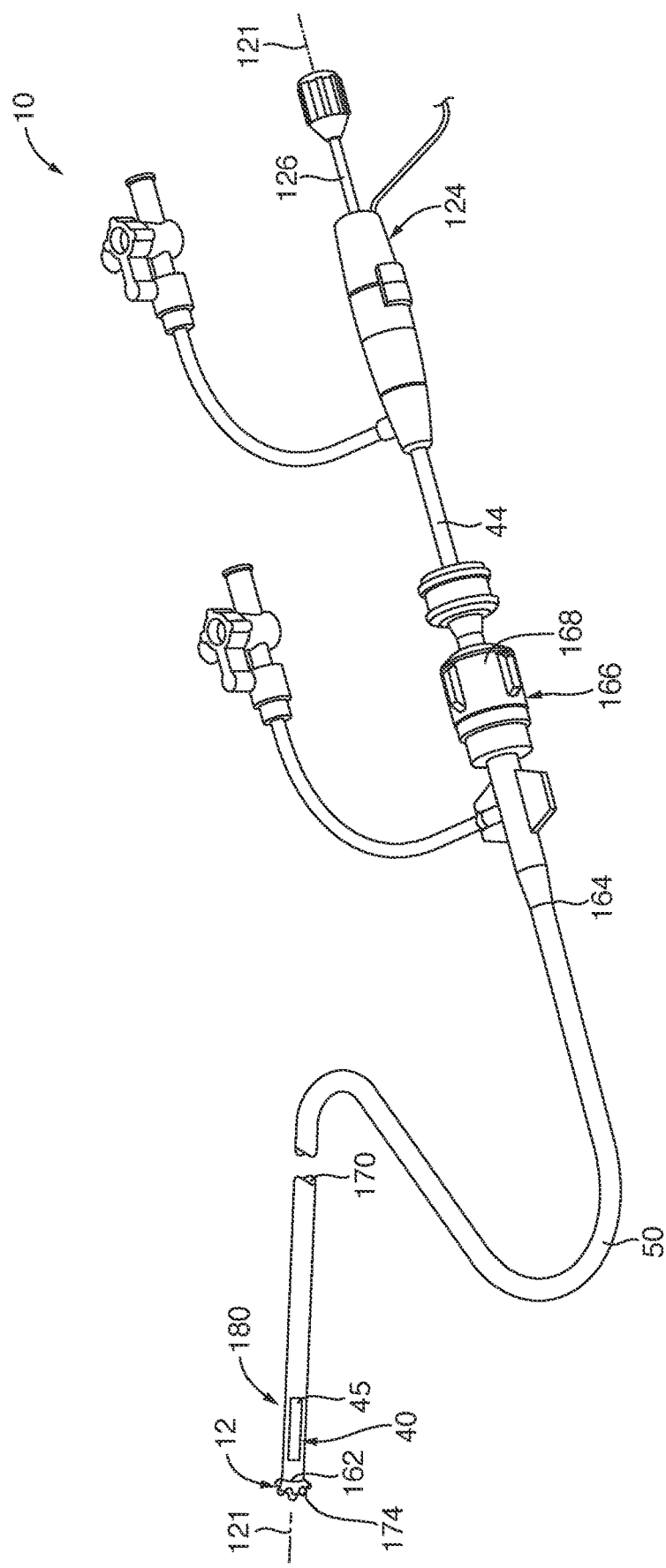
FIG. 3 is a perspective view of the medical device delivery system, depicting the medical device at least partially constricted within a sheath and coupled to a pusher catheter that extends through the sheath, according to one embodiment of the present invention.

With reference to FIG. 3, as previously set forth, the medical device delivery system 10 may include the sheath 50. Such sheath 50 may extend between a distal end 162 and a proximal end 164. The proximal end 164 of the sheath 50 may be associated with a sheath handle 166 and a valve 168. The sheath 50 may also define the central lumen 170 extending along the longitudinal length of the sheath 50, the central lumen 170 sized and configured to advance the medical device 12 and pusher catheter 44 therethrough. The medical device 12 may be constricted and advanced through the central lumen 170 to be positioned adjacent the distal end 162 of the sheath 50. In some embodiments, an atraumatic portion 174 or cushion portion of the occluder portion 132 (FIG. 4) of the medical device 12 may extend slightly distal from the distal end 162 of the sheath 50. As such, the atraumatic portion 174 of the medical device delivery system 10 may assist in minimizing the puncture of tissue in the heart or other anatomy prior to and during deployment of the medical device 12.

As previously set forth, the sheath 50 may include the third magnetic field location sensor 45 positioned along an end portion 180 of the sheath 50. Such third magnetic field location sensor 45 may include a single sensor or multiple sensors positioned along the end portion 180 of the sheath 50. As such, the one or more third magnetic field location sensors 45 may be positioned in a wall of the sheath 50 so as to be embedded therein and so as to be exposed along an exterior surface of the sheath 50. In another embodiment, the one or more third magnetic field location sensors 45 may be positioned along an inner surface of the end portion 180 of the sheath 50. In this manner, the one or more third magnetic field location sensors 45 of the sheath 50 may be employed with the medical system 14 (FIG. 1), similar to that of the first and second magnetic field location sensors previously described. As such, the one or more third magnetic field location sensors 45 of the sheath 50 may interact and cooperate with the medical system 14 to assist the physician with display information so that the physician can appropriately orient and position the end portion 180 of the sheath 50 in the left atrium as well as location and anatomical information as the sheath 50 is being advanced through the vasculature and/or in the heart prior to deploying the medical device 12 from the sheath 50.

Figure 4:
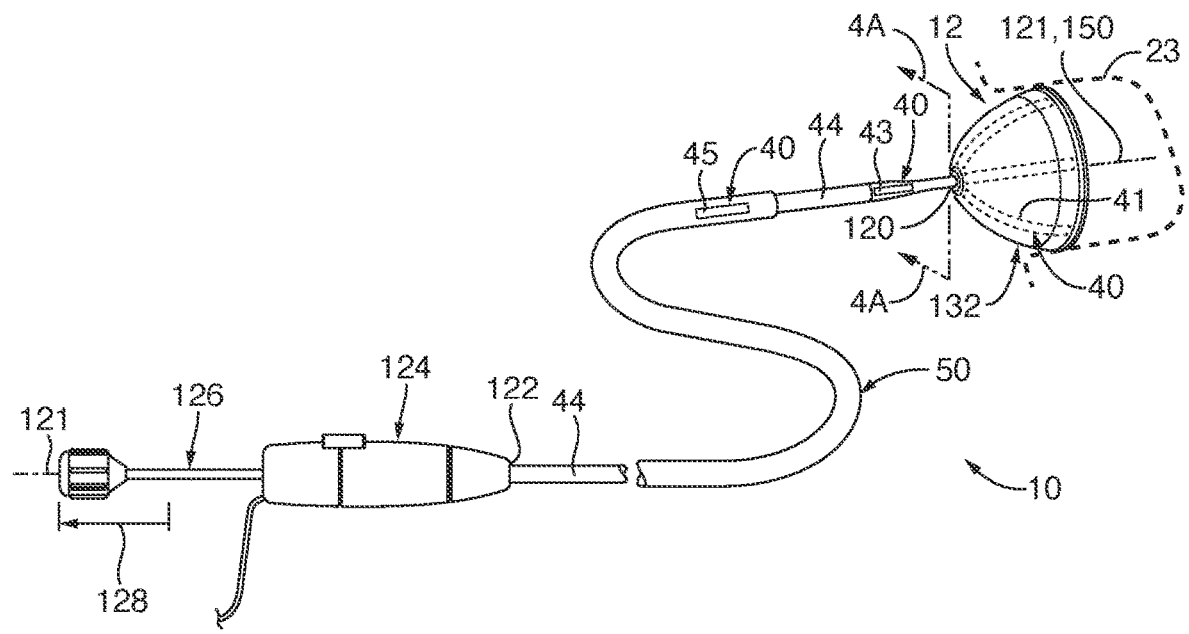
FIG. 4 is a perspective view of the medical device delivery system, depicting the medical device in a partially deployed position with the sheath withdrawn from the medical device, according to another embodiment of the present invention.
Figure 4A:
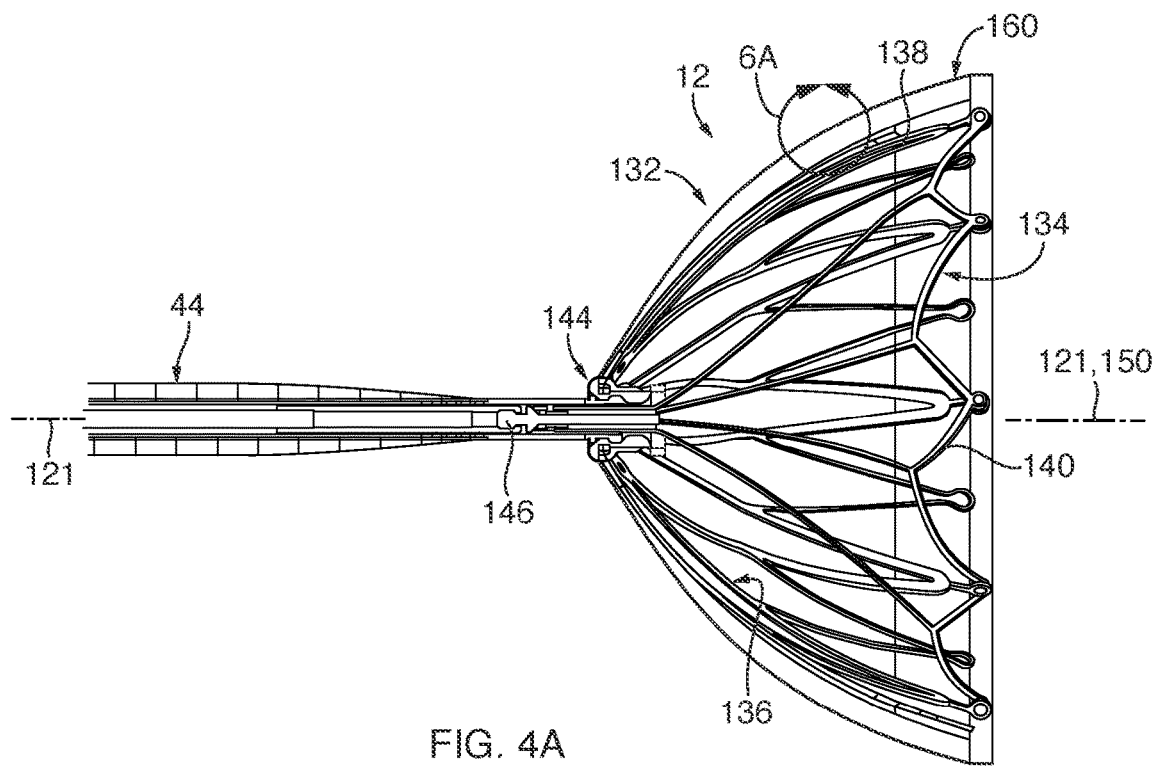
FIG. 4A is a cross-sectional view of the medical device coupled to the delivery system taken along section line 4A-4A in FIG. 4, according to another embodiment of the present invention.

Now with reference to FIGS. 1 and 4, upon the physician being satisfied with the position of the end portion 180 of the sheath 50 in the left atrium of the heart, the occluder portion 132 may be deployed from the distal end 162 of the sheath 50 by moving the sheath 50 proximally relative to the pusher catheter 44. As such, as the sheath 50 is moved proximally over the pusher catheter 44, the occluder portion 132 immediately self-expands to an occluder deployed position. Upon the occluder portion 132 of the medical device 12 being deployed from the sheath 50, the one or more first and/or second magnetic field location sensors 41, 43 may be employed in conjunction with the medical system 14 to assist the physician with the position and orientation of the deployed occluder portion 132 within the left atrium 29 of the heart 13. As set forth, the one or more first magnetic field location sensors 41 may be associated with the tissue growth member 160. In addition, the one or more second magnetic field location sensors 43 may be positioned along the distal end portion 42 of the pusher catheter 44. With the first and/or second magnetic field location sensors 41, 43 of the medical device 12 and pusher catheter 44 employed with the medical system 14, as previously described herein, the physician may obtain imaging information to assist the physician to effectively and safely position the deployed occluder portion 132 of the medical device 12 within, or adjacent to, the ostium 21 of the left atrial appendage 23 (as depicted in FIG. 4).

With respect to FIGS. 1, 4 and 5, once the physician is satisfied with the position and orientation of the deployed occluder portion 132 within the left atrial appendage 23, the physician may actuate the anchor portion 134 to the deployed position by moving the anchor actuator 126 distally. With the medical system 14 and the display information 36 provided via the sensors of the medical system 14, the physician may effectively view the position and orientation of the medical device 12 relative to the mapped anatomy so that, upon actuating the anchor portion 134 so that the anchor portion pivots and engages tissue with the tines 142 of the anchor portion 134, the physician can better understand if the medical device 12 is appropriately positioned and engaged with the tissue in the left atrial appendage 23 (as depicted in FIG. 5).

Figure 6A:
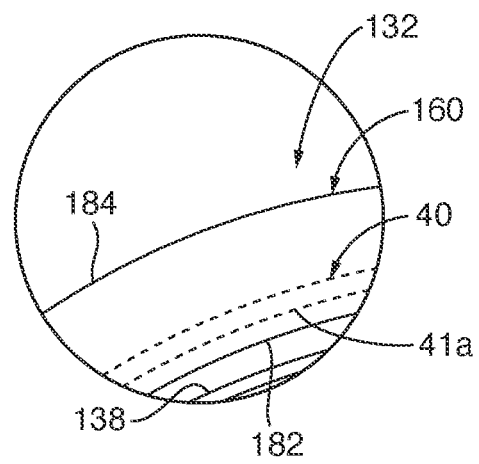
FIG. 6A is an enlarged view of a portion of the medical device taken from region 6A of FIG. 4A, depicting a magnetic field location sensor disposed within a tissue growth member of the medical device, according to another embodiment of the present invention.
Figure 6B:
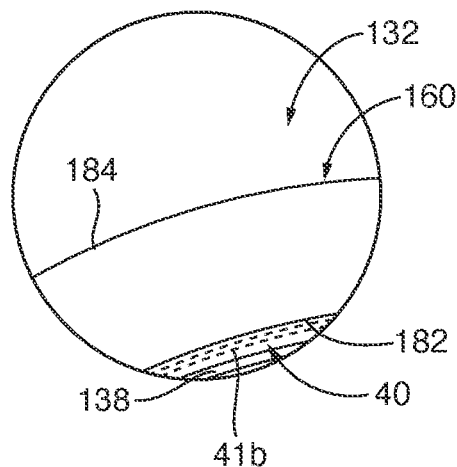
FIG. 6B is an enlarged view of another embodiment of a portion of the medical device, depicting the magnetic field location sensor positioned below the tissue growth member of the medical device, according to the present invention.
Figure 6C:
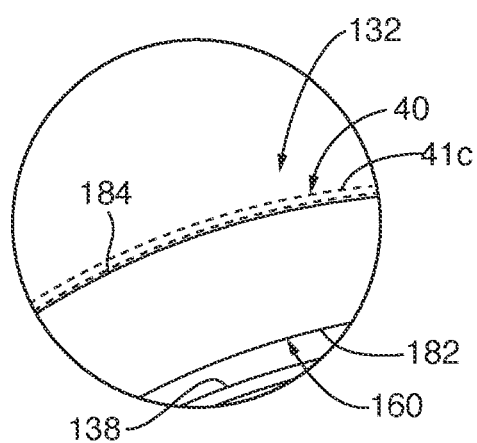
FIG. 6C is an enlarged view of another embodiment of a portion of the medical device, depicting the magnetic field location sensor positioned over the tissue growth member of the medical device, according to the present invention.

Now with reference to FIGS. 6A, 6B and 6C, various embodiments of the one or more magnetic field location sensors 40 positioned and/or integrated with the tissue growth member 160 of the medical device 12 are provided. For example, with respect to FIGS. 4 and 6A, the tissue growth member 160 may extend to define an inner external surface 182 and an outer external surface 184. The inner external surface 182 may extend alongside the occluder frame segments 138 of the occluder portion 132 of the medical device 12 and may be referenced as an inner portion of the tissue growth member 160. In this embodiment, the medical device 12 may include the one or more first magnetic field location sensors 41a positioned between the inner and outer external surfaces 182, 184 of the tissue growth member 160. In another embodiment, the inner portion of the tissue growth member 160 may be any portion inward of the outer external surface 184 of the tissue growth member 160. In another embodiment, the inner portion of the tissue growth member 160 may be between the inner and outer external surfaces 182, 184 of the tissue growth member 160. The tissue growth member 160 may extend with multiple polymeric layers such that the one or more first magnetic field location sensors 41a may be integrated with and embedded within the tissue growth member 160.

With respect to FIGS. 4 and 6B, another embodiment of one or more first magnetic field location sensors 41b positioned with the tissue growth member 160 of the medical device 12. In this embodiment, the one or more first magnetic field location sensors 41b may be positioned along the inner external surface 182 of the tissue growth member 160. In another embodiment, the one or more first magnetic field location sensors 41b may be partially embedded in the tissue growth member 160 along the inner external surface 182 thereof. In another embodiment, the one or more first magnetic field location sensors 41b may extend along the occluder frame segments 138 such that the tissue growth member 160 covers the one or more first magnetic field location sensors 41b. In another embodiment, the one or more first magnetic field location sensors 41b may be positioned adjacently along an inner portion, as previously set forth, of the tissue growth member 160.

With respect to FIGS. 4 and 6C, another embodiment of one or more first magnetic field location sensors 41c positioned with the tissue growth member 160 of the medical device 12. In this embodiment, the one or more first magnetic field location sensors 41c may be positioned along the outer external surface 184 of the tissue growth member 160. In another embodiment, the one or more first magnetic field location sensors 41c may be partially embedded within the outer external surface 184 of the tissue growth member 160 such that one side of the one or more first magnetic field location sensors 41c may be exposed along the outer external surface 184 of the tissue growth member 160. In another embodiment, the one or more first magnetic field location sensors may extend alongside an inner portion of the tissue growth member 160.

Now with reference again to FIG. 5, once the physician is satisfied with the engagement of the anchor portion 134 of the medical device 12 to tissue within the left atrial appendage 23 through, for example, a tug-test in combination to viewing display information 36 of the medical device 12 and anatomy via the display 18 of the medical system 14 (see FIG. 1), the physician can then prepare to permanently release the medical device 12 from the pusher catheter 44 in the anatomy, such as the left atrial appendage 23. As previously set forth in FIG. 1, the implantable medical device 12 having the one or more magnetic field location sensors 40 may be electrically interconnected to the control console 16 with a wire 46.

Figure 7:
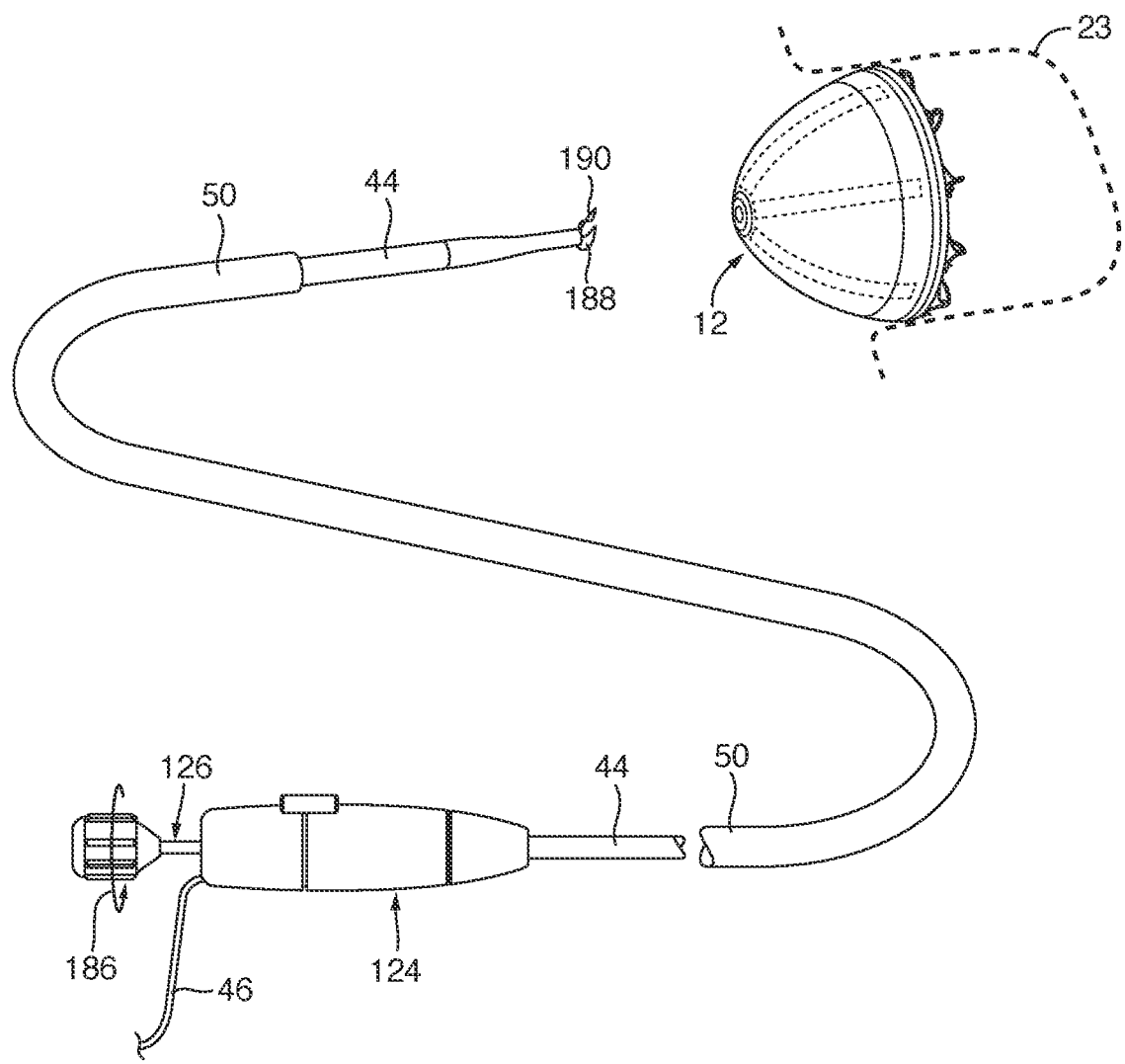
FIG. 7 is a perspective view of the medical device delivery system, depicting the medical device released from the delivery system, according to another embodiment of the present invention.

As such, with reference to FIG. 7, in a wired version of the implantable medical device 12, the medical device 12 may be released from the pusher catheter 44 by rotating the anchor actuator 126 extending from the pusher catheter handle 124, as shown by arrow 186. Such rotation may activate a release mechanism (not shown) to release the pusher catheter 44 from the primary and/or secondary hubs 144, 146 of the medical device 12. Further, such rotation may also deploy a cutting element 188 that may cut a distal wire portion 190 of the wire 46 adjacent the medical device 12. Upon the medical device being fully released by rotating the anchor actuator 126, the anchor actuator may be rotated back to its original position to reverse the cutting element 188 back into the pusher catheter 44 so that the pusher catheter 44 may be withdrawn through the sheath 50 and vasculature of the patient. In this manner, the electrical interconnection between the sensors of the medical device 12 and the control console 16 may be severed with a cutting element 188 so that the medical device 12 may be fully released from the medical device delivery system 10.

Figure 8:
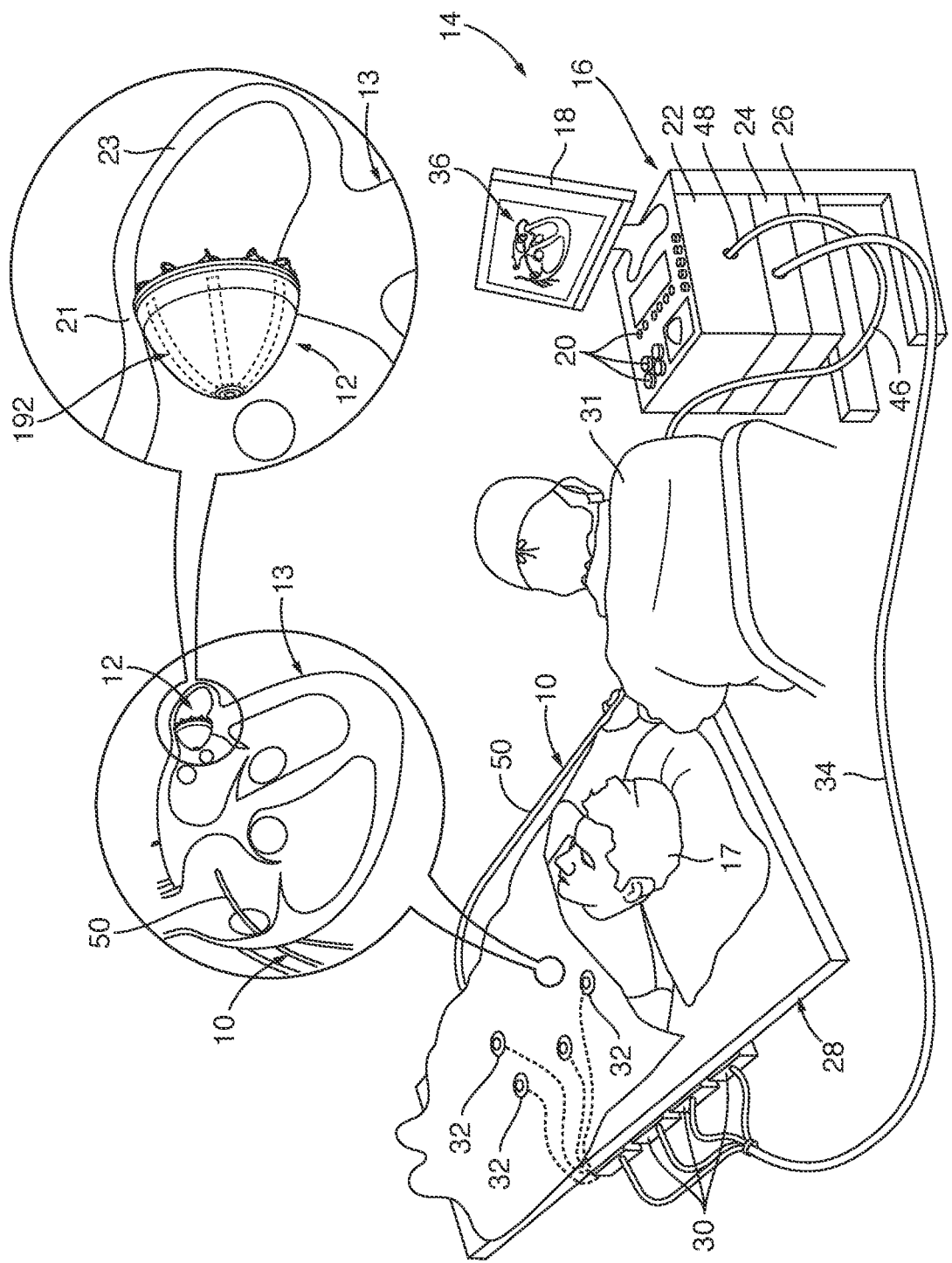
FIG. 8 is a perspective view that illustrates the medical system wirelessly coupled to an implanted medical device, depicting the delivery system being withdrawn from the heart, according to another embodiment of the present invention.

Now with reference to FIG. 8, in another embodiment, the medical device delivery system 10 may include one or more magnetic field location sensors 192 disposed with the medical device 12, but in this embodiment, the delivery system 10 does not require a cutting element for cutting a wire, as set forth in the previous embodiment. Rather, the one more magnetic field location sensors 192 may communicate with the medical system 14 in a wireless manner, as previously described herein. In this embodiment, the medical system may include each of the components set forth in FIG. 1, such as the control console 16 with the display 18, the input device 20, the driver circuit 22, the signal processor 24, and the memory 26. Further, the medical system 14 may include the patient platform 28, the field generators 30, and the body surface electrodes 32 that may be disposed on the skin of the patient 17 and each be coupled to the control console 16 with connector wire 34. Each of these components may function in a similar manner as described relative to FIG. 1. The medical device delivery system 10 of this embodiment may also include one or more magnetic field location sensors 40 positioned in the distal end portions of the pusher catheter 44 and/or the sheath 50 (see FIGS. 3-5) that may electrically communicate with the control console 16 with the wire 46 or such sensors may electrically communicate with the control console wirelessly. With this arrangement, upon the medical device 12 being implanted within the anatomy, such as the left atrial appendage 23 of the heart 13, the physician 31 may continue to obtain display information 36 from the one more magnetic field location sensors 192 of the implanted medical device 12 in conjunction with data obtained via the electrodes 32 and the field generators 30 and any other magnetic field location sensors 40 disposed in a medical device delivery system. In addition, even in follow-up visits with the patient, the physician may employ the medical system 14 and wirelessly activate the one or more magnetic field location sensors 192 disposed with the implanted medical device 12 to obtain display information 36 relating to the implanted medical device 12 so as to obtain useful information relating to the implanted medical device and how it may be integrating with the tissue to block-off the left atrial appendage 23. In this manner, the medical device delivery system 10 may include the one or more magnetic field location sensors 40, 192 (see FIGS. 3-5, and 8) at multiple locations to assist the physician 31, such as in the sheath 50, the pusher catheter 44, and/or the medical device 12, so that the physician can obtain display information 36 in real-time of the orientation and position of the medical device 12 relative to the anatomy of the heart 13 to assist the physician 31 to safely and effectively implant the medical device 12 in the anatomy of a patient, such as in the ostium 21 of the left atrial appendage 23 of the heart 13.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes incorporating any portion of one embodiment with another embodiment, all modifications, equivalents, and alternatives falling within the spirit and scope of the invention as defined by the following appended claims.

What is claimed is:

1. A medical system for generating three-dimensional imaging within a heart of a patient, the medical system comprising:
    a controller coupled to one or more magnetic field generators and a display, the one or more magnetic field generators configured to generate a magnetic field within the anatomy of the patient, the display for providing display information thereon;
    a sheath extending with a longitudinal length and a lumen defined along the longitudinal length of the sheath,
    a pusher catheter with a handle and an implantable medical device, the implantable medical device removably coupled from a distal end of the pusher catheter, the pusher catheter and the implantable medical device moveable through the lumen of the sheath such that the implantable medical device is moveable between a constricted position and an expanded position, the implantable medical device including a framework and a tissue growth member, the tissue growth member supported by frame segments of the framework, the tissue growth member configured to promote tissue in-growth; and
    one or more magnetic field location sensors coupled to the implantable medical device and operatively coupled to the controller, the one or more magnetic field location sensors configured to facilitate providing the three-dimensional imaging within the heart so as to be viewable on the display;

wherein the one or more magnetic field location sensors are fixed to the tissue growth member of the implantable medical device, the tissue growth member extending with an external surface and an inner portion, the external surface of the tissue growth member configured to directly contact tissue within the left atrial appendage, the one or more magnetic field location sensors positioned along the inner portion of the tissue growth member.

2. The medical system of claim 1, wherein the one or more magnetic field location sensors are directly positioned on at least one of the pusher catheter and the sheath.

3. The medical system of claim 1, wherein the one or more magnetic field location sensors are operatively coupled to the controller with at least one of a wire connection and a wireless connection.

4. The medical system of claim 1, wherein the handle of the pusher catheter is sized and configured to release the implantable medical device from the distal end of the pusher catheter to permanently implant the implantable medical device within the heart.

5. The medical system of claim 1, wherein, upon the implantable medical device being removed from the pusher catheter such that the implantable medical device is implanted in the heart, the one or more magnetic field location sensors coupled to the implantable medical device is activatable wirelessly.

6. A medical system for generating three-dimensional imaging within a heart of a patient, the medical system comprising:

a controller coupled to one or more magnetic field generators and a display, the one or more magnetic field generators configured to generate a magnetic field within the anatomy of the patient, the display for providing display information thereon;

a medical device delivery system including a sheath, a pusher catheter and an implantable medical device, the sheath extending with a central lumen sized and configured to advance the pusher catheter and the implantable medical device therethrough, the pusher catheter having a handle coupled to a proximal end of the pusher catheter, the implantable medical device removably coupled from a distal end of the pusher catheter, the implantable medical device including a framework and a tissue growth member, the tissue growth member supported by frame segments of the framework, the tissue growth member configured to promote tissue in-growth, the implantable medical device including one or more magnetic field location sensors fixed to the tissue growth member and operatively coupled to the controller, the one or more magnetic field location sensors configured to facilitate providing the three-dimensional imaging within the heart viewable on the display;

wherein the tissue growth member extends with an external surface and an inner portion, the external surface of the tissue growth member configured to directly contact tissue within the left atrial appendage, the one or more magnetic field location sensors positioned along the inner portion of the tissue growth member.

7. The medical system of claim 6, wherein the pusher catheter comprises a pusher catheter magnetic field location sensor, the pusher catheter magnetic field location sensor being coupled to the controller and positioned adjacent a distal end portion of the pusher catheter.

8. The medical system of claim 6, wherein the sheath comprises a sheath magnetic field location sensor, the sheath magnetic field location sensor being coupled to the controller and positioned adjacent a distal end portion of the sheath.

9. The medical system of claim 6, wherein the one or more magnetic field location sensors are operatively coupled to the controller with at least one of a wire connection and a wireless connection.

10. The medical system of claim 6, wherein the handle of the pusher catheter is sized and configured to release the implantable medical device from the distal end of the pusher catheter to permanently implant the implantable medical device within the heart.

11. The medical system of claim 6, wherein, upon the implantable medical device being removed from the pusher catheter such that the implantable medical device is implanted in the heart, the one or more magnetic field location sensors positioned with the implantable medical device is activatable wirelessly.

12. A method for obtaining three-dimensional imaging within a left atrium and left atrial appendage of a heart, the method comprising:

generating a magnetic field within the anatomy of a patient with one or more magnetic field generators positioned adjacent the patient;

advancing a medical device delivery system through a vasculature of the patient and toward the heart of the patient, the medical device delivery system sized and configured to deliver an implantable medical device in the left atrial appendage of the heart with a pusher catheter such that the implantable medical device includes a framework and a tissue growth member, the tissue growth member supported by frame segments of the framework, the tissue growth member configured to promote tissue in-growth;

activating one or more magnetic field location sensors coupled to the medical device delivery system for obtaining the three-dimensional imaging within the left atrium;

deploying the tissue growth member of the implantable medical device adjacent the left atrial appendage;

viewing the three-dimensional imaging of the left atrium on a display of a control console operatively coupled to the magnetic field generators and the medical device delivery system;

securing the implantable medical device to tissue with anchoring tines sized and configured to engage tissue such that the implantable medical device is positioned adjacent to or within the left atrial appendage of the heart; and releasing the pusher catheter of the delivery system from the implantable medical device to permanently leave the implantable medical device adjacent to or within the left atrial appendage of the heart;

wherein the deploying comprises deploying the implantable medical device with at least some of the one or more magnetic field location sensors fixed to an inner portion of the tissue growth member.

13. The method according to claim 12, wherein the activating comprises wirelessly activating the one or more magnetic field location sensors.

14. The method according to claim 12, wherein the activating comprises activating the one or more magnetic field location sensors directly positioned on at least one of the pusher catheter and a sheath of the medical device delivery system.

15. The method according to claim 12, wherein subsequent to the releasing comprises activating the one or more magnetic field location sensors fixed to the implantable medical device wirelessly.

\* \* \* \* \*